United States Patent [19]

Iwata

[11] Patent Number: 5,461,902
[45] Date of Patent: Oct. 31, 1995

[54] APPARATUS FOR THERMALLY CONTROLLING AN OXYGEN SENSOR OF INTERNAL COMBUSTION ENGINE

[75] Inventor: Yoichi Iwata, Susono, Japan

[73] Assignee: Toyota Jidosha Kabushiki Kaisha, Aichi, Japan

[21] Appl. No.: 318,103

[22] Filed: Oct. 5, 1994

[30] Foreign Application Priority Data

Oct. 12, 1993 [JP] Japan .................................. 5-254516

[51] Int. Cl.$^6$ ...................... G01N 27/16; G01N 27/407
[52] U.S. Cl. ........................................................... 73/23.32
[58] Field of Search .................................. 73/116, 118.1, 73/23.2, 23.31, 23.32

[56] References Cited

U.S. PATENT DOCUMENTS

| | | | |
|---|---|---|---|
| 4,251,225 | 2/1981 | Handa et al. | 73/23.2 |
| 4,291,572 | 9/1981 | Maurer et al. | 73/23.2 |
| 4,419,190 | 12/1983 | Dietz et al. | 204/1 T |
| 4,611,562 | 9/1986 | Nakano et al. | 73/23.32 |
| 4,732,128 | 3/1988 | Yoshioka et al. | 73/23.31 |
| 5,279,145 | 1/1994 | Suzuki | 73/23.31 |
| 5,327,780 | 7/1994 | Entenmann et al. | 73/118.1 |

FOREIGN PATENT DOCUMENTS

| | | |
|---|---|---|
| 60-17349 | 1/1985 | Japan . |
| 64-6691 | 2/1989 | Japan . |
| 2-2915 | 1/1990 | Japan . |
| 4-24657 | 4/1992 | Japan . |

Primary Examiner—Richard Chilcot
Assistant Examiner—George M. Dombroske
Attorney, Agent, or Firm—Oliff & Berridge

[57] ABSTRACT

An oxygen sensor heat controlling apparatus includes: a current-limiting type oxygen sensor whose electrical characteristic varies with a change in an oxygen concentration of exhaust gases from an internal combustion engine, and whose alternating current resistance varies with a change in an operating temperature of the sensor; a voltage source connected with the sensor through a resistor to supply a given voltage to the sensor; a differential amplifier having a first input connected with the sensor and a second input connected with the voltage source through the resistor, the amplifier producing at its output an output signal derived from the difference between the given voltage and an output voltage from the sensor, the output signal being representative of the oxygen concentration of the exhaust gases; a first closed loop circuit which connects the output of the amplifier with the first input of the amplifier via a first feedback resistor so as to control a current flow through the sensor; a second closed loop circuit which connects the output of the amplifier with the second input thereof via a second feedback resistor; a heater for heating the sensor; an oscillation detecting circuit for detecting occurrence of an oscillation at the output of the amplifier and for outputting a pulse when the occurrence of the oscillation is detected; and a current control circuit for applying current to the heater when the oscillation has not occurred, and for stopping the application of current to the heater in response to the pulse.

8 Claims, 4 Drawing Sheets

APPARATUS FOR THERMALLY CONTROLLING AN OXYGEN SENSOR OF INTERNAL COMBUSTION ENGINE

BACKGROUND OF THE INVENTION (1) Field of the Invention

The present invention generally relates to an oxygen sensor of an internal combustion engine, and more particularly to an apparatus for controlling the heating of a current-limiting type oxygen sensor which is adapted to determine the oxygen content in combustion exhaust gases and especially in the exhaust gases from internal combustion engines of automotive vehicles.

(2) Description of the Related Art

Generally, outputs of an oxygen sensor which determine the oxygen concentration of exhaust gases from an internal combustion engine vary depending on the temperature of a sensing portion to which the oxygen sensor is exposed. It has been proposed to heat the oxygen sensor and to control the heating of the oxygen sensor so that it will be operating at an essentially constant temperature.

U.S. Pat. No. 4,419,190 (corresponding to Japanese Published Patent Application No.4-24657) discloses a proposed apparatus to measure an operating temperature of a current-limiting type oxygen sensor. In the proposed apparatus, an ac signal from an ac voltage source is superimposed on a dc signal from a dc voltage source, and it is applied to two electrodes of a current-limiting type sensor, and the magnitude of output current flowing through the sensor is measured so that the operating temperature of the sensor which is highly dependent on the alternating current resistance of the sensor is determined. The proposed apparatus controls the heating of the sensor in accordance with the determined temperature of the sensor, so that it will be operating at an essentially constant temperature. The proposed apparatus will thus realize a device for controlling the heating of the current-limiting type oxygen sensor with no need for an additional temperature sensor, the temperature sensor used to sense the operating temperature of the oxygen sensor.

However, it is necessary that the proposed apparatus mentioned above uses an ac voltage source which generates an ac signal to be superimposed on the dc signal, in order to determine the operating temperature of the sensor. Also, it is necessary that the proposed apparatus includes a comparator to compare the amplitude of the alternating voltage from the ac voltage source with the amplitude of the alternating voltage from the sensor with a high accuracy. Thus, the proposed apparatus has a complicated circuit structure with additional circuit components, and the cost of manufacture will be increased.

SUMMARY OF THE INVENTION

Accordingly, it is a general object of the present invention to provide an improved oxygen sensor heat controlling apparatus in which the above-described problem is eliminated.

Another, more specific object of the present invention is to provide an oxygen sensor heat controlling apparatus which controls the heating of a current-limiting type oxygen sensor so as to maintain the operating temperature of the oxygen sensor at an essentially constant temperature level with no need for an ac voltage source or a temperature sensor.

Still another object of the present invention is to provide an oxygen sensor heat controlling apparatus which is simple and reliable and can determine the operating temperature of a current-limiting type oxygen sensor with no need for an ac voltage source or a temperature sensor, so as to suitably control the heating of the oxygen sensor.

The above-mentioned object of the present invention is achieved by an oxygen sensor heat controlling apparatus which includes: a current-limiting type solid electrolyte oxygen sensor whose electrical characteristic varies with a change in an oxygen concentration of exhaust gases from an internal combustion engine, and whose alternating current resistance varies with a change in an operating temperature of the sensor, the sensor having two electrodes; a voltage source connected with one of the electrodes of the sensor through a first resistor to supply a given voltage to the sensor; a differential amplifier having a first input connected with the other electrode of the sensor and a second input connected with the voltage source through the first resistor, and the differential amplifier producing at its output an output signal derived from the difference between the given voltage from the voltage source and an output voltage from the sensor, the output signal being representative of the oxygen concentration of the exhaust gases; a first closed loop circuit having a first feedback resistor which connects the output of the differential amplifier with the first input of the differential amplifier so as to control a current flow through the sensor; a second closed loop circuit having a second feedback resistor which connects the output of the differential amplifier with the second input of the differential amplifier; a heating element for heating the sensor in accordance with an applied current; an oscillation detecting circuit for detecting whether or not an oscillation at the output of the differential amplifier has occurred, and for outputting a pulse signal when the occurrence of the oscillation is detected; and a current control circuit for applying current to the heating element to heat the sensor when the oscillation has not occurred, and for stopping the application of current to the heating element in response to the pulse signal from the oscillation detecting circuit, so as to maintain an operating temperature of the sensor at an essentially constant temperature level.

According to the present invention, it is possible to control the heating of the oxygen sensor so as to maintain the operating temperature of the oxygen sensor at an essentially constant temperature level with no need for an ac voltage source or a temperature sensor. It is possible to realize an oxygen sensor heat controlling apparatus which is simple and reliable and determines the operating temperature of the oxygen sensor with no need for an ac voltage source or a temperature sensor.

BRIEF DESCRIPTION OF THE DRAWINGS

The other objects, features and advantages of the present invention will be more apparent from the following detailed description when read in conjunction with the accompanying drawings in which.

DESCRIPTION OF THE PREFERRED EMBODIMENTS

A description will now be given of an engine system to which the present invention is applied, with reference to FIG.2.

Figure 2:
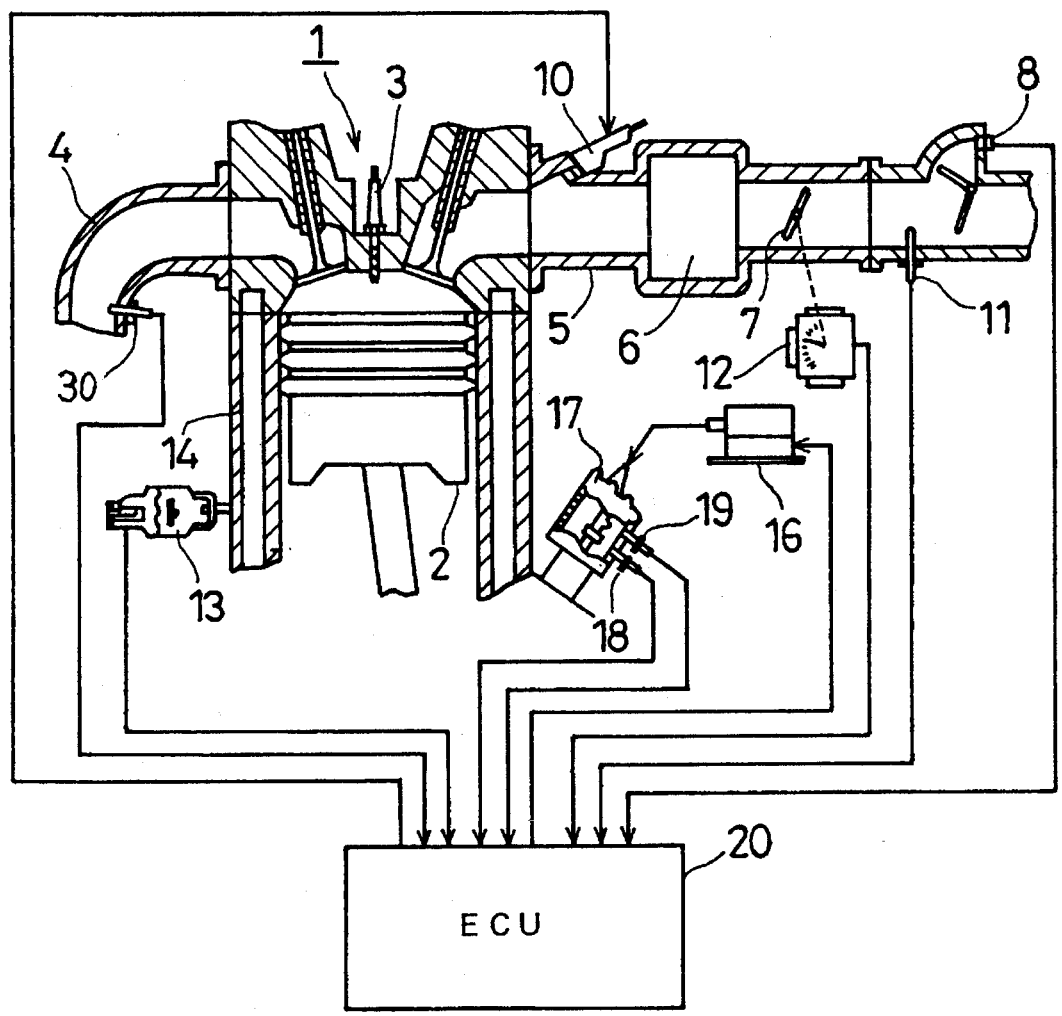
FIG.2 is a diagram showing an engine system to which the present invention is applied.

In FIG.2, the engine system includes an internal combustion engine 1, a piston 2, a spark plug 3, an exhaust manifold 4, an intake manifold 5, a surge tank 6 to absorb the pulsation of intake air flow, a throttle valve 7 to adjust the flow rate of intake air, and an air flow meter 8 to measure the flow rate of intake air. The internal combustion engine is, for example, a four-cylinder gasoline engine. In the engine system, a current-limiting type oxygen sensor 30 which is adapted to measure the oxygen concentration in exhaust gases from the engine 1 is arranged on the exhaust manifold 4, and a fuel injection valve 10 which is adapted to inject fuel into the intake air flowing into the engine 1 is arranged on the intake manifold 5. The oxygen sensor 30 outputs an oxygen content signal indicating the measured oxygen concentration in exhaust gases. An air temperature sensor 11 which outputs an air temperature signal indicating the temperature of intake air is arranged on an intake pipe in the vicinity of the air flow meter 8, the intake pipe being connected to the surge tank 6. A throttle position sensor 12 which outputs a signal indicating a throttle valve position of the throttle valve 7 is coupled to the throttle valve 7. A knock sensor 13 which outputs a signal indicating occurrence of a knocking operation of the engine 1 is arranged on a cylinder block 14 of the engine 1.

An igniter 16 generates a high voltage causing the spark plug 3 to spark, and supplies the high voltage to a distributor 17. The distributor 17 distributes the high voltage to the spark plug of each of the cylinders in accordance with the rotating angle of a crankshaft (not shown) of the engine 1. A crank angle sensor 18 outputs a rotational angle signal NE, the rotational angle signal NE having twenty four pulses for every two revolutions of the crankshaft. Two revolutions of the crankshaft correspond to one revolution of a shaft of the distributor 17. A cylinder discriminating sensor 19 outputs a pulse signal G indicating the engine rotation each time one revolution of the shaft of the distributor 17 takes place.

An electronic control unit (ECU) 20 is provided in the engine system in FIG.2. Various detection signals output by the above-mentioned sensors in the engine system are inputs of the ECU 20 during operation of the engine system. The ECU 20 determines an ignition time for the igniter 16 and a fuel injection time for each fuel injection valve 10 based on the detection signals, and outputs an ignition time signal and a fuel injection signal to the igniter 16 and the fuel injection valve 10, respectively.

Next, a description will be given of an oxygen sensor heat controlling apparatus in a first embodiment of the present invention with reference to FIGS. 1, 3 and 4.

Figure 1:
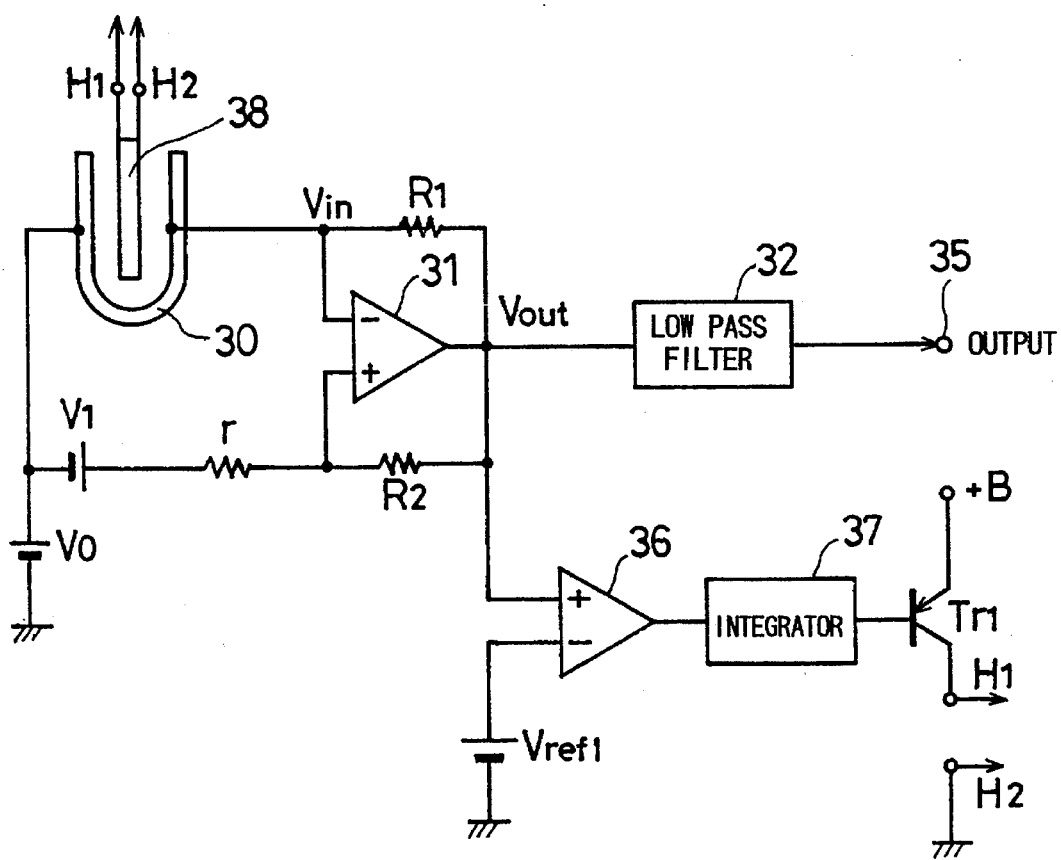
FIG.1 is a circuit diagram showing an oxygen sensor heat controlling apparatus in a first embodiment of the present invention.

In FIG. 1, the current-limiting type oxygen sensor 30 has two electrodes: one being connected to a dc voltage source Vo, and the other being connected to a first input (or an inverted input) of a differential amplifier 31. A second input (or a non-inverted input) of the differential amplifier 31 is connected to a first dc voltage source V1 via a first resistor "r". The first input and the second input of the differential amplifier 31 are indicated by the negative sign "−" and the positive sign "+" in FIG. 1, respectively. The first dc voltage source V1 is connected to the dc voltage source Vo. An output of the differential amplifier 31 is connected to the first input thereof via a first feedback resistor R1, and it is connected to the second input thereof via a second feedback resistor R2. Hereinafter, a closed loop circuit including the first feedback resistor R1 connected between the first input of the differential amplifier 31 and the output thereof is called a first feedback loop, and a closed loop circuit including the second feedback resistor R2 connected between the second input of the differential amplifier 31 and the output thereof is called a second feedback loop.

Also, the output of the differential amplifier 31 is connected to a low pass filter 32 so that a voltage Vout output by the differential amplifier 31 is present at a terminal 35 at the output of the low pass filter 32. The low pass filter 32 suppresses the ac component of the voltage Vout at the output of the differential amplifier 32, and only the dc component of the voltage Vout passes through the low pass filter 32. Thus, a voltage that is representative of the oxygen concentration in the exhaust gases from the engine which is supplied from the oxygen sensor 30 can be obtained from the terminal 35 for indication or for application for further control functions within the engine system in FIG.2.

The output of the differential amplifier 31 is further connected to a first input (or a non-inverted input) of a comparator 36. A second input (or an inverted input) of the comparator 36 is connected to a reference voltage source so that a reference voltage Vref1 from the reference voltage source is applied to the second input of the comparator 36. The first input of the comparator 36 is indicated by the positive sign "+" in FIG. 1, and the second input thereof is indicated by the negative sign "−" in FIG. 1. The comparator 36 compares the voltage Vout from the output of the differential amplifier 31 with the reference voltage Vref1 from the reference voltage source, and outputs a pulse signal indicating the result of the comparison. The comparator 36 forms an oscillation detecting circuit in the oxygen sensor heat controlling apparatus. An output of the comparator 36 is connected to an integrator representative 37 so that an integral of the pulses output by the comparator 36 is produced by the integrator 37. An output of the integrator 37 is connected to a base of a PNP transistor Tr1 so that the PNP transistor Tr1 is turned on or off in accordance with the output signal of the integrator 37. As shown, an output of the PNP transistor Tr1 is connected to a heating element 38 which is provided for heating the oxygen sensor 30. When the transistor Tr1 is turned on, the application of current to the heating element 38 is allowed to continue. On the other hand, when the transistor Tr1 is turned off, the application of current to the heating element 38 is stopped. The integrator 37 and the PNP transistor Tr1 form a current application control unit which controls the application of current to the heating element 38 in the oxygen sensor heat controlling apparatus.

The current-limiting type oxygen sensor 30 described above has a solid electrolyte body (for example, made of zirconium dioxide), and two electrodes connected to different surface regions of the zirconium dioxide are formed on the solid electrolyte body. The electrodes are oxygen-gas pervious, and have a measuring voltage applied thereto. Depending on the oxygen concentration in the gas to which the oxygen sensor 30 is exposed, a higher or lower diffusion limiting current will be established, and the current is limited by the diffusion rate of the oxygen molecules which reach the electrodes.

Figure 3:
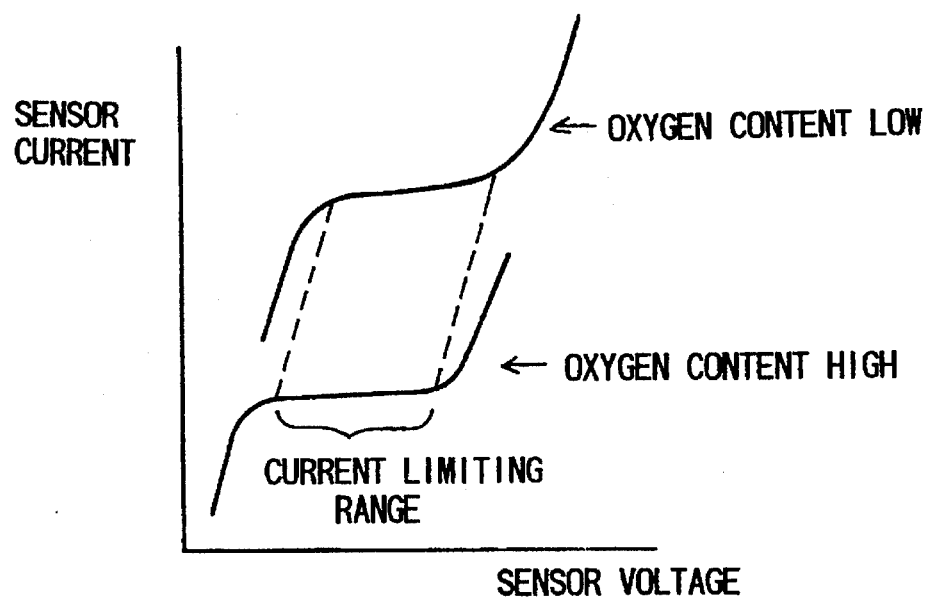
FIG.3 is a graph of voltage vs. current of a current-limiting type oxygen sensor for a low oxygen content level and a high oxygen content level.

The oxygen sensor 30 described above, when exposed to the exhaust gas from the engine, has an operating characteristic as shown in FIG.3. In FIG.3, changes in the current measured through the oxygen sensor 30 with respect to changes in the applied dc voltage are shown. For any given oxygen level, there can be found a value of saturation current in which the current is steady or constant over a certain measuring voltage region applied to the electrodes. As shown, for a relatively high oxygen content level, the saturation current value is found to be relatively small. On the other hand, for a relatively low oxygen content level, the saturation current value mentioned above will be increased to a level greater than that of the relatively high oxygen content case. That is, the oxygen sensor 30 has an operating characteristic wherein the saturation current value, corresponding to the current-limiting range, varies proportionally with changes in oxygen concentration of exhaust gases from the engine.

In addition, the current-limiting type oxygen sensor 30 has an operating characteristic wherein the current varies proportionally with changes in ac voltage applied to the electrodes of the oxygen sensor 30. Generally, the alternating current (ac) resistance Rs of the oxygen sensor 30 has been found to be less than the dc resistance of the sensor. The ac resistance Rs of the oxygen sensor 30 is highly temperature dependent, and if the operating temperature T of the oxygen sensor 30 rises, the ac resistance Rs thereof becomes smaller, as shown in FIG.4.

Next, a description will be given of the operation of the oxygen sensor heat controlling apparatus in the first embodiment. As described above, the ac resistance of the oxygen sensor 30 varies with changes in the oxygen concentration of exhaust gases from the engine and with changes in the operating temperature of the oxygen sensor 30.

For the sake of better understanding of the present invention, the following equations are defined with respect to voltages at the circuit components of each of the first feedback loop and the second feedback loop in the oxygen sensor heat controlling apparatus in FIG. 1:

$$Vin = V1' + (Vout - V1') \cdot r/(R2+r)$$

$$Vin = Vo + V2 + (Vout - Vo - V2) \cdot Rs/(R1+Rs)$$

where:

V1' is the offset voltage (V1'=V1+Vo),

Vin is the voltage at the first input of the differential amplifier 31;

Vout is the voltage at the output of the differential amplifier 31; and

V2 is the voltage between the electrodes of the oxygen sensor 30.

If a small change in the voltage Vin of the differential amplifier 31 with respect to each of the first and second feedback loops is taken, the following equations are derived from the above equations since the voltages V1' and Vo are constant.

$$\Delta Vin = 568 \, Vout \cdot r/(R2+r)$$

$$\Delta Vin = (\Delta Vout - \Delta V2) \cdot Rs/(R1+Rs) + \Delta V2$$

By solving these equations, $$\Delta Vout = \Delta V2 \cdot R1 \cdot (R2+r)/(Rs \cdot R2 - R1 \cdot r) \quad (1)$$

Therefore, when the oxygen concentration in exhaust gases from the engine changes, or when the operating temperature of the oxygen sensor 30 changes, the ac resistance of the oxygen sensor 30 varies as defined in the equation (1) above. Especially when Rs=r·R1/R2, an oscillation at the output of the differential amplifier 31 takes place. The values of the resistances of the resistors r, R1 and R2 and the value of the ac resistance of the oxygen sensor 30 are preset such that the oscillation condition Rs=r·R1/R2 is met at a relatively high temperature of the oxygen sensor 30.

Figure 4:
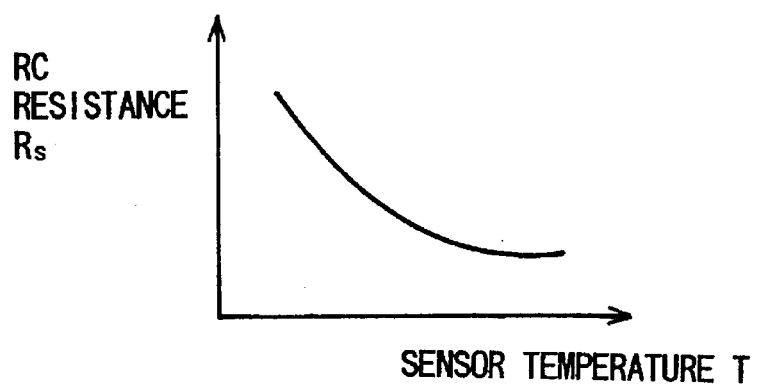
FIG.4 is a graph of temperature vs. ac resistance of a current-limiting type oxygen sensor.

As shown in FIG.4, if the operating temperature T of the oxygen sensor 30 rises, the ac resistance Rs thereof becomes smaller. When the operating temperature of the oxygen sensor 30 is relatively low, the ac resistance Rs of the oxygen sensor 30 is too high to induce an oscillation at the output of the differential amplifier 31. At this time, the voltage Vout at the output of the differential amplifier 31 is detected by the comparator 36 to be lower than the reference voltage Vref1. The comparator 36 thus outputs low-level pulses to the integrator 37, and the transistor Tr1 is turned on so that the application of current to the heating element 38 is allowed to continue.

As the oxygen sensor 30 is heated by the heating element 38, the operating temperature of the oxygen sensor 30 rises and the ac resistance Rs of the oxygen sensor 30 falls to a level that satisfies the oscillation condition Rs=r·R1/R2 mentioned above. Thus, an oscillation at the output of the differential amplifier 31 takes place. The voltage Vout of the differential amplifier 31 is increased with the oscillation, and it is detected to be higher than the reference voltage Vref1 by the comparator 36. The comparator 36 outputs high-level pulses to the integrator 37, and the transistor Tr1 is turned off and the application of current to the heating element 38 is stopped.

The operating temperature of the oxygen sensor 30 falls during the stop of the application of current to the heating element 38, and the ac resistance Rs of the oxygen sensor 30 rises and the output of the differential amplifier 31 does not oscillate. Thereafter, the level of the output signal of the integrator 37 becomes lower, and the transistor Tr1 is turned on to allow the application of current to the heating element 38 and the oxygen sensor 30 is heated by the heating element 38. The above procedure is repeated while the oxygen sensor 30 operates.

In the first embodiment described above, an oscillation at the output of the differential amplifier 31 is induced by a small change in the ac resistance of the current-limiting type oxygen sensor by using the first and second feedback loops. The small change in the ac resistance of the oxygen sensor 30 is made due to changes in the oxygen concentration of the exhaust gases from the engine or due to changes in the oxygen sensor temperature. Once the oscillation at the output of the differential amplifier 31 is detected, the application of current to the heating element 38 is stopped. Therefore, it is possible to control the heating of the current-limiting type oxygen sensor so as to maintain the operating temperature of the oxygen sensor at an essentially constant temperature level with no need for an ac voltage source or a temperature sensor.

Figure 5:
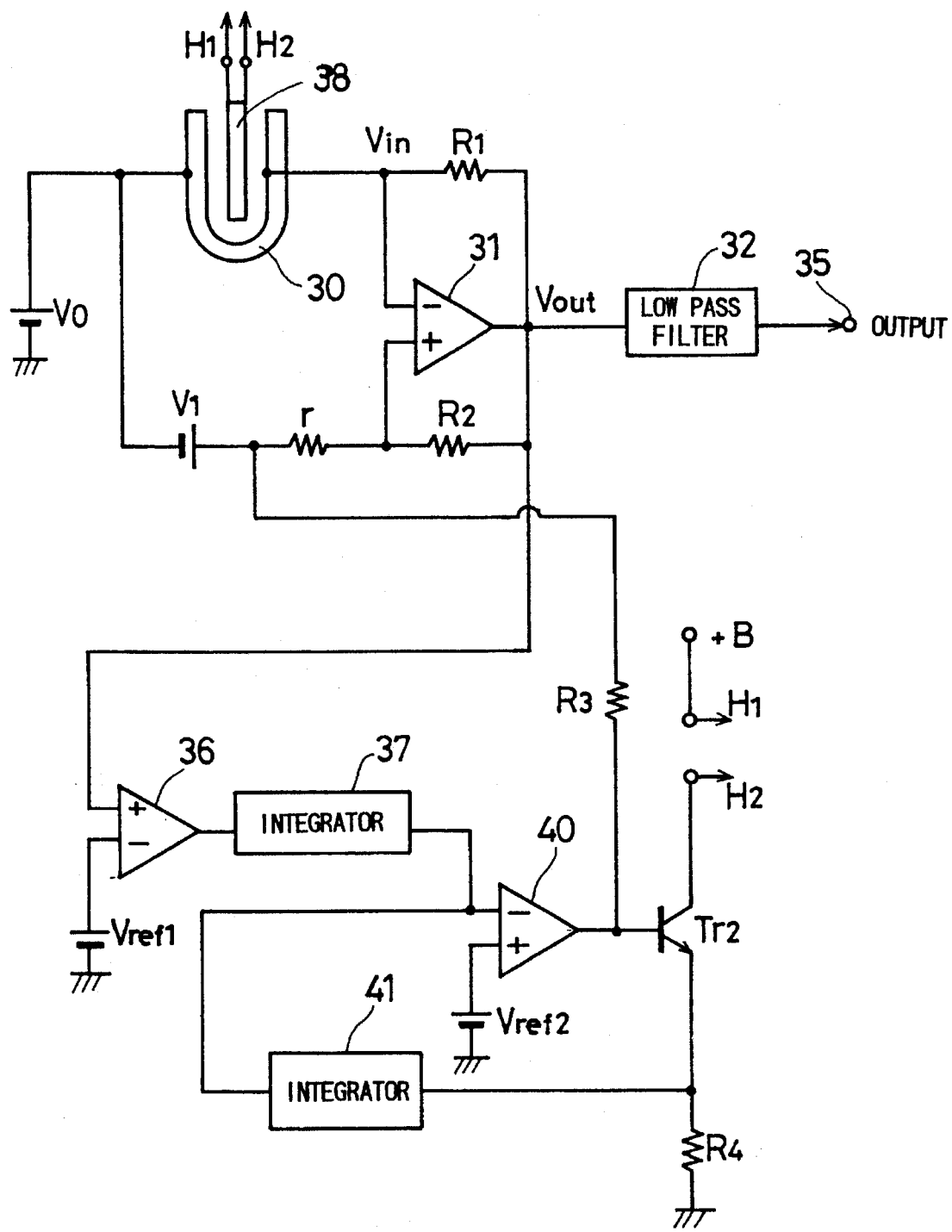
FIG.5 is a circuit diagram showing an oxygen sensor heat controlling apparatus in a second embodiment of the present invention.

Next, a description will be given of an oxygen sensor heat controlling apparatus in a second embodiment of the present invention, with reference to FIG.5. In FIG.5, the parts which are the same as corresponding parts shown in FIG.1 are designated by the same reference numerals, and a description thereof will be omitted.

In FIG.5, the oxygen sensor heat controlling apparatus includes first and second comparators 36 and 40, first and second integrators 37 and 41, and an NPN transistor Tr2.

The first comparator 36 and the first integrator 37 are the same as those of the first embodiment in FIG.1. An output of the first integrator 37 is connected to a first input (or an inverted input "−") of the second comparator 40, and a reference voltage source Vref2 is connected to a second input (or a non-inverted input "+") of the second comparator 40. An output of the second comparator 40 is connected to a base of the NPN transistor Tr2, and it is also connected to an output of the first dc voltage source V1 via a third resistor R3.

The heating element 38 which is provided to heat the oxygen sensor 30 is connected at one end (H1) to a dc voltage source "B" and connected at the other end (H2) to a collector of the NPN transistor Tr2. An emitter of the NPN transistor Tr2 is grounded via a fourth R4, and it is connected to an input of the second integrator 41. The second integrator 41 integrates voltage signals output from the emitter of the NPN transistor Tr2. The output signal of the second integrator 41 is added to the output signal of the first integrator 37, and it is supplied to the first input of the second comparator 40.

When the operating temperature of the oxygen sensor 30 is relatively low, the ac resistance Rs of the oxygen sensor 30 is too high to induce an oscillation at the output of the differential amplifier 31. At this time, the voltage Vout at the output of the differential amplifier 31 is detected by the first comparator 36 to be lower than the reference voltage Vref1. The first comparator 36 thus outputs low-level pulses to the first integrator 37. The output signal of the first integrator 37 is supplied to the inverted input of the second comparator 40. The second comparator 40 outputs high-level pulses to the transistor Tr2, and the transistor Tr2 is turned on so that the application of current to the heating element 38 is allowed to continue.

As the oxygen sensor 30 is heated by the heating element 38 to a higher temperature, the operating temperature of the oxygen sensor 30 rises. The ac resistance Rs of the oxygen sensor 30 falls to a level that satisfies the oscillation condition Rs=r·R1/R2 mentioned above. Thus, an oscillation at the output of the differential amplifier 31 takes place at that time. The voltage Vout at the output of the differential amplifier 31 rises with the oscillation, and the first comparator 36 detects that the voltage Vout is higher than the reference voltage Vref1. The first comparator 36 outputs high-level pulses to the first integrator 37, and the level of the output voltage of the first integrator 37 rises and becomes higher than the reference voltage Vref2. The second comparator 40 outputs low-level pulses to the transistor Tr2, and the transistor Tr2 is turned off to stop the application of current to the heating element 38.

In the second embodiment described above, regardless of whether or not an oscillation at the output of the differential amplifier 31 takes place, the second integrator 41 produces an integral of the voltage output from the emitter of the transistor Tr2. That is, the second integrator 41 outputs the average of the current flowing through the heating element 38 with respect to time. As the average of the current flowing through the heating element 38 increases, the level of the output signal of the second integrator 41 rises. When the level of the output signal of the second integrator 41 becomes higher than the reference voltage Vref2, the second comparator 40 outputs low-level pulses to the base of the transistor Tr2 so that the transistor Tr2 is turned off, thus preventing the application of an excessive amount of current to the heating element 38. Therefore, it is possible to maintain the operating temperature of the oxygen sensor 30 at an essentially constant temperature level.

The operating temperature of the oxygen sensor 30 falls during the stop of the application of current to the heating element 38, and the ac resistance Rs of the oxygen sensor 30 rises and the output of the differential amplifier 31 does not oscillate. Thereafter, the level of the output signal of the first integrator 37 becomes lower. When the second integrator 41 outputs low-level signals, the second comparator 40 outputs high level pulses to the base of the transistor Tr2 so that the transistor Tr2 is turned on and the application of current to the heating element 38 is allowed to continue. The oxygen sensor 30 is heated by the heating element 38 to a higher temperature. The above procedure is repeated when the oxygen sensor 30 operates.

In the second embodiment described above, the output of the second comparator 40 is connected to the output of the first dc voltage source V1 via the third resistor R3. When the output signal of the second comparator 40 changes from low level to high level or vice versa, the voltage at the second input (the non-inverted input) of the differential amplifier 31 is responsive to the change of the output signal of the second comparator 40. This makes the oxygen sensor heat controlling apparatus in the second embodiment useful and effective in a case in which an oscillation at the output of the differential amplifier 31 is not quickly induced by a small change in the ac resistance of the oxygen sensor 30. For example, when the oxygen concentration of the exhaust gases from the engine is unchanged or constant, the ac resistance of the oxygen sensor 30 remains unchanged.

Concerning the above case, the following equations are defined with respect to voltages at the circuit components of each of the first feedback loop and the second feedback loop in the oxygen sensor heat controlling apparatus in FIG.5. In this case, the voltage V2 between the electrodes of the oxygen sensor 30 is constant but the voltage V1 varies in response to the output of the second comparator 40.

$$Vin = V1' + (Vout - V1') \cdot r/(R2+r)$$

$$Vin = Vo + V2 + (Vout - Vo - V2) \cdot Rs/(R1+Rs)$$

where:

V1' is the offset voltage (V1'=V1+Vo);

Vin is the voltage at the first input of the differential amplifier 31; and

Vout is the voltage at the output of the differential amplifier 31.

If a small change in the voltage Vin of the differential amplifier 31 with respect to each of the first and second feedback loops is taken, the following equations are derived from the above equations since the voltages V2 and Vo are constant but the voltage V1' is variable.

$$\Delta Vin = \Delta V1' + (\Delta Vout - \Delta V1') \cdot r/(R2+r)$$

$$\Delta Vin = \Delta Vout \cdot Rs/(R1+Rs)$$

By solving these equations, $$\Delta Vout = \Delta V1' \cdot R2 \cdot (R1+Rs)/(Rs \cdot R2 - R1 \cdot r) \quad (2)$$

Therefore, when the oxygen concentration in exhaust gases from the engine changes, or when the operating temperature of the oxygen sensor 30 changes, the ac resistance Rs of the oxygen sensor 30 varies as defined in the equation (2) above. Also, in the second embodiment, when the ac resistance Rs falls to a level that satisfies the condition Rs=r·R1/R2, the output of the differential amplifier 31 oscillates. Similarly to the first embodiment, the values of the resistances of the resistors r, R1 and R2 and the value of the ac resistance of the oxygen sensor 30 are preset such that the oscillation condition $Rs=r \cdot R1/R2$ is satisfied at a relatively high temperature of the oxygen sensor 30.

Further, the present invention is not limited to the above-described embodiments, and variations and modifications may be made without departing from the scope of the present invention.

What is claimed is:

1. An apparatus for thermally controlling an oxygen sensor of an internal combustion engine, comprising:
   - a current-limiting type solid electrolyte oxygen sensor whose electrical characteristic varies with a change in an oxygen concentration of exhaust gases from an internal combustion engine, and whose alternating current resistance varies with a change in an operating temperature of said sensor, said sensor having two electrodes;
   - a voltage source connected with one of said electrodes of the sensor through a first resistor to supply a given voltage to the sensor;
   - a differential amplifier having a first input connected with the other electrode of the sensor and a second input connected with the voltage source through the first resistor, said differential amplifier producing at its output an output signal derived from the difference between said given voltage from the voltage source and an output voltage from the sensor, and said output signal being representative of the oxygen concentration of the exhaust gases;
   - a first closed loop circuit having a first feedback resistor which connects the output of the differential amplifier with the first input of the differential amplifier so as to control a current flow through the sensor;
   - a second closed loop circuit having a second feedback resistor which connects the output of the differential amplifier with the second input of the differential amplifier;
   - heating means for heating the sensor in accordance with an applied current;
   - oscillation detecting means for detecting whether or not an oscillation at the output of the differential amplifier has occurred, and for outputting a pulse when the occurrence of the oscillation is detected; and
   - current control means for applying current to said heating means to heat the sensor when said oscillation has not occurred, and for stopping the application of current to said heating means in response to the pulse from said oscillation detecting means, so as to maintain an operating temperature of the sensor at an essentially constant temperature level.

2. An apparatus according to claim 1, wherein said oscillation detecting means comprises a comparator which has a first input connected with the output of the differential amplifier and a second input connected with a first reference voltage source, said comparator outputting a pulse when a voltage at the output of the differential amplifier rises and becomes higher than a given reference voltage from the first reference voltage source.

3. An apparatus according to claim 1, further comprising a low pass filter connected with the output of the differential amplifier to suppress alternating current components and to pass through direct current components of the output signal from the differential amplifier, so that a signal representative of the oxygen concentration of the exhaust gases is output.

4. An apparatus according to claim 1, wherein an oscillation at the output of the differential amplifier occurs when an alternating current resistance Rs of the sensor changes to a value that satisfies the condition $Rs=r \cdot R1/R2$ where r is a resistance of the first resistor, R1 is a resistance of the first feedback resistor, and R2 is a resistance of the second feedback resistor.

5. An apparatus according to claim 1, wherein said current means comprises an integrator which outputs an integral representative of pulses output from said oscillation detecting means, and a transistor which selectively allows or inhibits the application of current to the heating means in response to the integral of the pulses from said integrator.

6. An apparatus according to claim 1, further comprising oscillation means which varies the voltage at the second input of the differential amplifier in association with changes in the average of current flowing through said heating means.

7. An apparatus according to claim 6, wherein said oscillation means comprises a comparator having a first input connected with said current control means via an integrator and having a second input connected with a reference voltage source, and an output of said comparator being connected with a switching unit of the current control means and with the second input of the differential amplifier via the first resistor.

8. An apparatus according to claim 6, wherein an oscillation at the output of the differential amplifier occurs when an alternating current resistance Rs of the sensor changes to a value that satisfies the equation $Rs=r \cdot R1/R2$ where r is a resistance of the first resistor, R1 is a resistance of the first feedback resistor, and R2 is a resistance of the second feedback resistor.

* * * * *